(12) United States Patent
Lagrange et al.

(10) Patent No.: US 7,326,257 B2
(45) Date of Patent: *Feb. 5, 2008

(54) COMPOSITION FOR DYEING KERATINOUS FIBERS COMPRISING AT LEAST ONE AZODIAZINE DIRECT DYE WHICH IS NON-AMINATED AT THE 7-POSITION AND DYEING METHOD USING SAID AT LEAST ONE AZODIAZINE DIRECT DYE

(75) Inventors: Alain Lagrange, Coupvray (FR); Frédéric Guerin, Paris (FR); Sylvain Kravtchenko, Asnières (FR)

(73) Assignee: L'Oreal, Paris (FR)

( * ) Notice: Subject to any disclaimer, the term of this patent is extended or adjusted under 35 U.S.C. 154(b) by 161 days.

This patent is subject to a terminal disclaimer.

(21) Appl. No.: 10/902,087

(22) Filed: Jul. 30, 2004

(65) Prior Publication Data

US 2005/0183210 A1   Aug. 25, 2005

Related U.S. Application Data

(60) Provisional application No. 60/509,946, filed on Oct. 10, 2003.

(30) Foreign Application Priority Data

Jul. 30, 2003  (FR) .................................. 03 50385

(51) Int. Cl.
*A61K 7/13* (2006.01)

(52) U.S. Cl. .................. 8/405; 8/406; 8/407; 8/408; 8/409; 8/410; 8/411; 8/412; 8/421; 8/425; 8/657; 8/689; 544/249

(58) Field of Classification Search ............ 8/405, 8/406, 407, 409, 410, 411, 412, 421, 425, 8/657, 689; 544/249
See application file for complete search history.

(56) References Cited

U.S. PATENT DOCUMENTS 2,528,378 A   10/1950  Mannheimer 2,781,354 A   2/1957  Mannheimer
4,395,301 A * 7/1983  Bauer et al. ............. 156/307.5

FOREIGN PATENT DOCUMENTS

| DE | 197 46 137 | 4/1999 |
|----|-----------|--------|
| EP | 1 166 754 | 1/2002 |
| FR | 1 285 848 | 4/1961 |

OTHER PUBLICATIONS

STIC Search Report dated Aug. 3, 2006.*
English language Derwent Abstract of DE 197 46 137, Apr. 22, 1999.
French Search Report of French Patent Application No. 0350385, Apr. 22, 2004.
"Handbook of Surfactants", M.R. Porter, Ed. Blackie & Son, Glasgow & London, 1991, 116-178.

* cited by examiner

*Primary Examiner*—Eisa Elhilo
(74) *Attorney, Agent, or Firm*—Finnegan, Henderson, Farabow, Garrett & Dunner, LLP

(57) ABSTRACT

Disclosed herein is a composition for dyeing keratinous fibers, comprising at least one direct dye corresponding to the following formula (I):

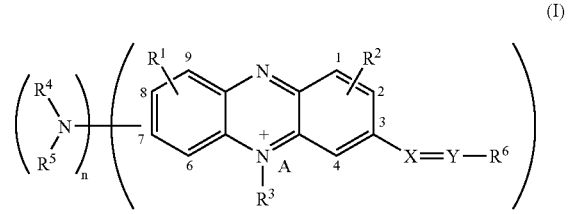

in which $R^1$ and $R^2$ may be chosen from hydrogen atoms; $R^3$ may be a phenyl group, n may chosen from 0 and 1; $R^4$ and $R^5$ may be alkyl groups having 1 to 6 carbon atoms; $R^6$ may be chosen from phenol groups and aniline groups; X and Y may represent nitrogen atoms, wherein the group —$NR^4R^5$ may occupy a position chosen from the 1-, 6-, 8-, and 9-position when n is equal to 1; and A is an anionic counterion. Further disclosed herein are methods for dyeing keratinous fibers using these direct dyes.

36 Claims, No Drawings

COMPOSITION FOR DYEING KERATINOUS FIBERS COMPRISING AT LEAST ONE AZODIAZINE DIRECT DYE WHICH IS NON-AMINATED AT THE 7-POSITION AND DYEING METHOD USING SAID AT LEAST ONE AZODIAZINE DIRECT DYE

This application claims benefit of U.S. Provisional Application No. 60/509,946, filed Oct. 10, 2003.

Disclosed herein are compositions for dyeing keratinous fibers, such as human keratinous fibers, for example hair, comprising at least one direct dye belonging to the family of azodiazine compounds.

Also disclosed herein is the use of compounds of the azodiazine family as direct dyes in compositions for dyeing keratinous fibers.

Further disclosed herein are methods for dyeing keratinous fibers using such compositions.

To dye keratinous fibers, such as the hair, it is known to use dyeing compositions containing oxidation dye precursors (such as ortho- or para-phenylenediamines, and ortho- or para-aminophenols, generally called "oxidation bases") and optionally couplers (e.g., meta-phenylenediamines, meta-aminophenols, and meta-diphenols, also called color modifiers). Oxidation dye precursors may be colorless or faintly colored precursors which, when combined with oxidizing products (such as hydrogen peroxide) may give rise, through an oxidation process, to colored and dyeing compounds.

However, methods for oxidation dyeing may have the following disadvantages:
  because of the use of oxidizing products such as hydrogen peroxide, they may cause degradation of the keratinous fiber and irritation of the scalp; or
  they may generate a fast color of the fibers, which may change over time, and they often cause selectivity in the color of the fiber, that is to say differences in color along the same keratinous fiber.

To minimize the above-mentioned disadvantages, it has been proposed to have recourse to methods of direct dyeing through the use of direct dyes, said methods comprising dyeing the hair by causing a colored molecule (the direct dye) to penetrate, by diffusion, into the hair without the use of hydrogen peroxide.

However, such methods have generally proved unsatisfactory for at least the following reasons:
  they may cause insufficient color fastness, wherein the color fades after a few shampooings; or
  they may also cause selectivity in the color of the fibers, that is to say differences in color along the same keratinous fiber.

A need therefore exists for a composition for dyeing keratinous fibers, which is not overly selective, can give a large variety of colors, can give intense colors, and additionally makes it possible to give a fast fiber color which changes little over time.

Thus, as disclosed herein, it has been discovered that certain azodiazine compounds incorporated in compositions for dyeing keratinous fibers may make it possible to overcome at least one of the disadvantages encountered in prior art and may make it possible, for example, to obtain a range of highly varied colors, a low selectivity, and a good level of fastness.

One embodiment disclosed herein is a composition comprising at least one dye chosen from the compounds of the following formula (I):

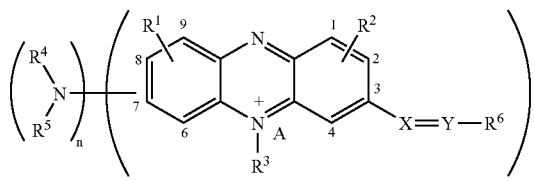

in which:
  $R^1$ and $R^2$, independently of each other, are chosen from:
    hydrogen;
    alkyl groups having 1 to 6 carbon atoms, optionally substituted with at least one group chosen from hydroxyl groups, amino groups, halogen groups, $C_1$ to $C_3$ alkoxy groups, and aryl groups;
    aryl groups having 6 to 18 carbon atoms, optionally substituted with at least one group chosen from amino groups, hydroxyl groups, $C_1$ to $C_3$ alkoxy groups, and $C_1$ to $C_6$ alkyl groups;
    carboxyalkyl groups having 1 to 6 carbon atoms; and
    sulphoalkyl groups having 1 to 6 carbon atoms;
  $R^3$ is chosen from optionally substituted alkyl groups having 1 to 6 carbon atoms, alkenyl groups having 2 to 20 carbon atoms, and cyclic groups having 5 to 100 carbon atoms, wherein said cyclic groups are aromatic or non-aromatic and optionally comprise at least one heteroatom and at least one unsaturated bond, and further wherein said cyclic group is optionally substituted with at least one group chosen from hydroxyl groups, cyano groups, halogen groups, amino groups, aryl groups, alkoxy groups having 1 to 4 carbon atoms, and alkyl groups having 1 to 4 carbon atoms;
  $R^6$ is chosen from monocyclic groups and polycyclic groups, wherein said monocyclic groups and polycyclic groups have 5 to 100 carbon atoms and optionally have at least one heteroatom and at least one unsaturated bond, and further wherein said monocyclic and polycyclic groups are optionally substituted with at least one group chosen from hydroxyl groups, cyano groups, halogen groups, amino groups, aryl groups, alkoxy groups having 1 to 4 carbon atoms, and alkyl groups having 1 to 4 carbon atoms;
  X and Y, independently of each other, are chosen from nitrogen and groups CR', wherein R' is chosen from hydrogen and alkyl groups having 1 to 6 carbon atoms;
  A is an anionic counterion; and
  n is chosen from 0 and 1;
  wherein when n is equal to 1, the group of formula $R^4R^5N$— occupies a position chosen from the 1-, 6-, 8-, and 9-positions on formula (I) and $R^4$ and $R^5$, independently of each other, are chosen from hydrogen, aryl groups having 1 to 6 carbon atoms, and alkyl groups having 1 to 6 carbon atoms, wherein said aryl groups and alkyl groups are optionally substituted with at least one group chosen from hydroxyl groups, cyano groups, halogen groups, amino groups, aryl groups, and alkoxy groups having 1 to 4 carbon atoms.

As used herein, the expression alkyl group is generally understood to mean a linear or branched alkyl group having 1 to 6 carbon atoms, for example a group chosen from methyl, ethyl, n-propyl, i-propyl, n-butyl, i-butyl, and t-butyl groups.

As used herein, the expression alkoxy group is generally understood to mean an —O-alkyl group, wherein the term alkyl is as defined above.

As used herein, the expression amino group is generally understood to mean a group of formula —$NH_2$, optionally substituted on the nitrogen atom with one or two substituents such as alkyl groups having 1 to 6 carbon atoms.

As used herein, the expression alkenyl group is generally understood to mean a linear or branched alkenyl group having 2 to 20 carbon atoms.

Examples of alkenyl groups are vinyl, allyl, and cyclohexenyl groups.

As used herein, the expression aryl group is generally understood to mean a monocyclic or polycyclic hydrocarbon aromatic group having 6 to 18 carbon atoms, such as phenyl groups and naphthyl groups. This group may be optionally substituted with groups chosen from amino groups, hydroxyl groups, alkoxy groups having 1 to 3 carbon atoms, and alkyl groups having 1 to 6 carbon atoms. Examples of substituted aryl groups are for example 2-tolyl, 3-tolyl, and 4-tolyl groups.

As used herein, the expression carboxyalkyl group is generally understood to mean an alkyl group as defined above, containing at the end a group —$CO_2H$, such as a group chosen from carboxymethyl groups —$CH_2$—$CO_2H$ and carboxyethyl groups —$(CH_2)_2$—$CO_2H$.

As used herein, the expression sulphoalkyl group is generally understood to mean an alkyl group as defined above, containing a sulphur atom forming a bridge between the above-mentioned alkyl group and the tricyclic unit of the compounds of formula (I).

As used herein, the expression anionic counterion is generally understood to mean an anion capable of neutralizing the positive charge carried by the positively charged nitrogen atom of the tricyclic unit of the compounds of formula (I). This counterion may be chosen from halide counterions (such as chloride, bromide, and iodide), sulphate counterions, methosulphate counterions, phosphate counterions, and tosylate counterions.

As used herein, the expression heteroatom is generally understood to mean an atom other than a carbon atom, such as atoms chosen from oxygen, nitrogen, and sulphur atoms.

As disclosed herein, $R^3$ may represent an alkyl group substituted with at least one group chosen, for example, from hydroxyl groups, cyano groups, halogen groups, amino groups, aryl groups, and alcoxy groups having 1 to 4 carbon atoms. $R^3$ may also be chosen from alkenyl groups, as defined above, and cyclic groups having 5 to 100 carbon atoms, wherein said cyclic groups are aromatic or nonaromatic, optionally comprising at least one heteroatom and at least one unsaturated bond, and further wherein said cyclic group is optionally substituted. When $R^3$ is a cyclic group, it may be an aryl group having 6 to 18 carbon atoms, optionally substituted with at least one substituent chosen from hydroxyl groups, cyano groups, halogen groups, amino groups, alkoxy groups having 1 to 4 carbon atoms, and alkyl groups having 1 to 4 carbon atoms. By way of example, $R^3$ may represent an optionally substituted phenyl group.

According to the present disclosure, $R^6$ may be chosen from monocyclic groups having 5 to 100 carbon atoms and polycyclic groups having 5 to 100 carbon atoms, wherein said monocyclic groups and polycyclic groups optionally comprising at least one heteroatom and at least one unsaturated bond, and further wherein said monocyclic groups and polycyclic groups are optionally substituted. For example, $R^6$ may represent an aryl group having 6 to 18 carbon atoms, optionally substituted with at least one substituent chosen from hydroxyl groups, cyano groups, halogen groups, amino groups, alkoxy groups having 1 to 4 carbon atoms, and alkyl groups having 1 to 4 carbon atoms. By way of example, $R^6$ may be chosen from optionally substituted phenol groups and aniline groups, such as aniline groups optionally substituted on at least one of the nitrogen atom and the benzene ring.

When the phenol group is substituted, it may be substituted for example with at least one group chosen from cyano groups, halogen groups, amino groups, aryl groups, alkoxy groups having 1 to 4 carbon atoms, and alkyl groups having 1 to 4 carbon atoms.

When the group $R^6$ is an aniline group, it may be substituted on the nitrogen atom by one or two groups, said groups being, for example, alkyl groups, which may themselves also be substituted for example with at least one hydroxyl group and on the benzene ring with at least one group chosen from cyano groups, halogen groups, amino groups, aryl groups, alkoxy groups, and alkyl groups having 1 to 4 carbon atoms.

According to the present disclosure, X and Y, independently of each other, may be chosen from nitrogen and groups CR', wherein R' is chosen from hydrogen and alkyl groups having 1 to 6 carbon atoms. For example, X and Y may each represent a nitrogen atom.

When n is equal to 0, the compounds of formula (1) correspond to the following formula:

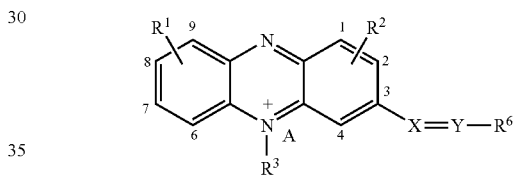

wherein $R^1$, $R^2$, $R^3$, $R^6$, X, and Y are as defined above. In this case, $R^1$ may occupy a position chosen from the 6-, 7-, 8-, and 9-positions, and $R^2$ may occupy a position chosen from the 1-, 2-, and 4-positions.

When n is equal to 1, the compounds of formula (I) correspond to the following formula:

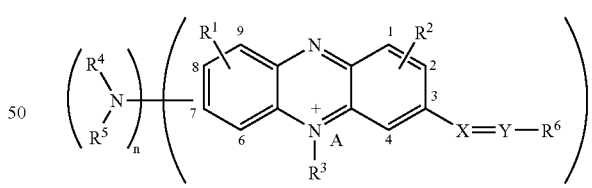

wherein $R^1$, $R^2$, $R^3$, $R^6$, X, and Y are as defined above.

In this case, the group $R^4R^5N$— may occupy a position chosen from the 1-, 6-, 8-, and 9-positions.

When the group $R^4R^5N$— occupies the 6-, 8-, or 9-position, the group $R^1$ may respectively occupy the 7-, 8-, or 9-position (when $R^4R^5N$— occupies the 6-position); the 6-, 7-, or 9-position (when $R^4R^5N$— occupies the 8-position); and the 6-, 7-, or 8-position (when $R^4R^5N$— occupies the 9-position).

When the group $R^4R^5N$— occupies the 1-position, the group $R^2$ may occupy a position chosen from the 2- and 4-positions.

As compounds of formula (I) which can be used in the context of the present disclosure, mention may be made of the following compounds corresponding to the following formulae (II), (III), and (IV) for which the anionic counterion A is as defined above:

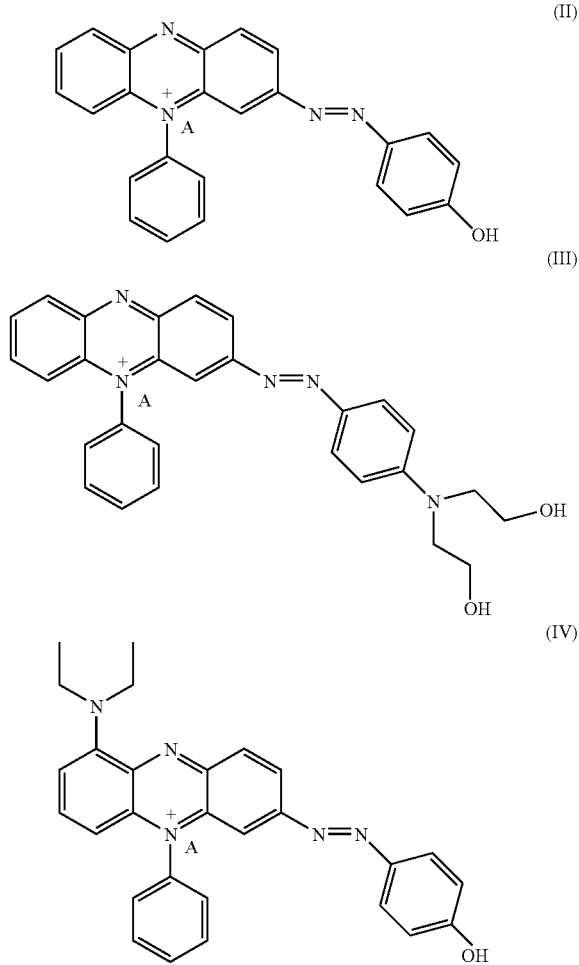

In certain embodiments, A is a chloride anion.

The dyes disclosed herein may be obtained by conventional synthesis schemes, such as those described in French Patent Application FR 1285848.

The compounds of formula (I) may be defined as direct dyes, that is to say that they do not require development with an appropriate agent, unlike oxidation dyes, which require development with at least one oxidizing agent.

The dyes disclosed herein may make it possible to obtain intense dyes on natural or optionally sensitized hair.

These dyes may also make it possible to obtain varying glints which are chromatic or dark, are very intense, are not very selective, and exhibit good fastness.

For example, the dyes disclosed herein may make it possible to obtain neutral grey and black glints which change little over time.

The amount of the at least one dye of formula (I) present in a dyeing composition as disclosed herein may range from 0.001 to 20% by weight, such as from 0.01 to 10% by weight, or from 0.1 to 5% by weight, relative to the total weight of the dyeing composition.

The dyeing composition according to certain embodiments may comprise an aqueous medium comprising water or a mixture of water and at least one cosmetically acceptable organic solvent. There may be mentioned, by way of examples of cosmetically acceptable organic solvents, alcohols such as ethyl alcohol, isopropyl alcohol, benzyl alcohol, polyols, polyol ethers, alkanes, ketones, and mixtures thereof.

In addition, the composition may comprise at least one other direct dye different from the compounds of formula (I) as defined above. These direct dyes may be chosen from the direct dyes conventionally used in direct dyeing, wherein this at least one direct dye may be chosen from nonionic, cationic, and amphoteric direct dyes. There may be mentioned, among these dyes, commonly used aromatic and/or nonaromatic dyes such as nitro dyes, methines, azomethines, styriles, triarylmethanes, diarylmethanes, azo dyes, anthraquinone dyes, naphthoquinone dyes, porphyrins, tetraphenylporphyrins, metalloporphyrins, phthalocyanines, carotenoid natural dyes, terpenoid natural dyes, flavonoid natural dyes, and fluorescent dyes such as fluorescein, rhodamine, and coumarin.

The composition disclosed herein may additionally comprise at least one oxidation base optionally combined with at least one coupler conventionally used for oxidation dyeing.

By way of examples of oxidation bases, mention may be made of para-phenylenediamines, bisphenylalkylenediamines, para-aminophenols, ortho-aminophenols, and heterocyclic bases such as diaminopyrazoles.

The combined couplers may, for example, be chosen from meta-phenylenediamine couplers, meta-aminophenol couplers, meta-diphenol couplers, naphthalenic couplers, and heterocyclic couplers.

In addition to the dyes, the dyeing composition of the invention may also comprise customary additives for dyeing compositions, wherein these additives may be chosen from at least one of surfactants, thickening agents, antioxidants, sequestering agents, dispersing agents, hair conditioners, preservatives, opacifying agents, acidifying agents, basifying agents, and perfumes.

It is understood that persons skilled in the art will make an appropriate choice of these additives so that the advantageous properties of the composition which are inherent to the presence of the compounds of formula (I) as defined above are not impaired by the above-mentioned additives.

The surfactants which may be present in the composition may be chosen from anionic, nonionic, amphoteric, and cationic surfactants.

Anionic, nonionic, amphoteric, and cationic surfactants which are suitable for use in the compositions disclosed herein may, for example, include the following:

Anionic Surfactants:

By way of examples of anionic surfactants which can be used, alone or as mixtures, mention may be made of salts, such as alkali metal salts (e.g., sodium salts, magnesium salts, ammonium salts, amine salts, amino alcohol salts, and the like) of the following compounds: alkyl sulphates, alkyl ether sulphates, alkyl amidoether sulphates, alkyl aryl polyether sulphates, monoglyceride sulphates, alkyl sulphonates, alkyl phosphates, alkyl amide sulphonates, alkyl aryl sulphonates, α-olefin sulphonates, paraffin sulphonates, ($C_6$-$C_{24}$)alkyl sulphosuccinates, ($C_6$-$C_{24}$)alkyl ether sulphosuccinates, ($C_6$-$C_{24}$)alkyl amide sulphosuccinates, ($C_6$-$C_{24}$) alkyl sulphoacetates, ($C_6$-$C_{24}$)acyl sarcosinates, and ($C_6$-$C_{24}$)acyl glutamates.

There may also be mentioned ($C_6$-$C_{24}$)alkyl polyglycoside carboxylic esters such as alkyl polyglucoside citrates, alkyl polyglucoside tartrates, alkyl polyglucoside sulphosuccinates, and alkyl polyglucoside sulphosuccinamates; acyl isethionates, and N-acyltaurates, wherein the alkyl or acyl radical of all these compounds may have 12 to 20 carbon atoms, and the aryl radical may be a group chosen from phenyl and benzyl groups.

Mention may also be made of the salts of fatty acids such as the salts of oleic, ricinoleic, palmitic, and stearic acids; acids of copra oil, acids of hydrogenated copra oil; acyl lactylates whose acyl radical has 8 to 20 carbon atoms; alkyl D-galactoside uronic acids and their salts; polyoxyalkylenated ($C_6$-$C_{24}$)alkyl ether carboxylic acids; polyoxyalkylenated ($C_6$-$C_{24}$)alkyl amidoether carboxylic acids and their salts, such as those having 2 to 50 alkylene oxide groups, such as ethylene oxide and mixtures thereof.

Nonionic Surfactants:

Nonionic surfactants are compounds which are well known per se (see for example the "Handbook of Surfactants", M. R. PORTER, Ed. Blackie & Son, Glasgow and London, 1991, 116-178) and their is optional in the context of the present disclosure.

Thus, used alone or as mixtures, they may, for example, be chosen from alcohols; α-diols; polyethoxylated and polypropoxylated alkylphenols having a fatty chain having, for example, 8 to 18 carbon atoms, wherein the number of ethylene oxide or propylene oxide groups may range, for example, from 2 to 50; copolymers of ethylene oxide and propylene oxide; condensates of ethylene oxide and propylene oxide with fatty alcohols; polyethoxylated fatty amides, such as those having from 2 to 30 mol of ethylene oxide; polyglycerolated fatty amides containing on average from 1 to 5, such as from 1.5 to 4, glycerol groups; oxyethylenated fatty acid esters of sorbitan containing from 2 to 30 mol of ethylene oxide; fatty acid esters of sucrose; fatty acid esters of polyethylene glycol; alkyl polyglycosides; derivatives of N-alkyl glucamine and amine oxides such as ($C_{10}$-$C_{14}$)alkyl amine oxides; and N-acylaminopropylmorpholine oxides.

Amphoteric Surfactants:

The amphoteric (or zwitterionic) surfactants, whose nature is optional in the context of the present disclosure, may be chosen, for example, alone or as mixtures, from the derivatives of aliphatic secondary or tertiary amines whose aliphatic radical is a linear or branched chain having 8 to 18 carbon atoms and comprising at least one water-solubilizing anionic group, for example a group chosen from carboxylate, sulphonate, sulphate, phosphate, and phosphonate groups.

There may also be mentioned ($C_8$-$C_{20}$)alkyl betaines, sulphobetaines, ($C_8$-$C_{20}$)alkyl amido($C_1$-$C_6$)alkyl betaines, and ($C_8$-$C_{20}$)alkyl amido($C_1$-$C_6$)alkyl sulphobetaines.

Among the amine derivatives, there may be mentioned for example the compounds marketed by the company Rhodia Chimie under the trade name Miranol®, which are described, for example, in U.S. Pat. Nos. 2,528,378 and 2,781,354 and which are classified in the CTFA Dictionary, 5$^{th}$ edition, 1993, under the names "disodium cocoamphodiacetate", "disodium lauroamphodiacetate", "disodium caprylamphodiacetate", "disodium caryloamphodiacetate", "disodium cocoamphodipropionate", "disodium lauroamphodipropionate", "disodium caprylamphodipropionate", "disodium capryloamphodipropionate", "lauroamphodipropionic acid", and "cocoamphodipropionic acid".

Cationic Surfactants:

As cationic surfactants which may be used alone or as mixtures, there may be mentioned the salts of optionally polyoxyalkylenated primary, secondary, and tertiary fatty amines; quaternary ammonium salts such as tetraalkylammonium, alkylamidoalkyltrialkylammonium, trialkylbenzylammonium, trialkylhydroxyalkylammonium and alkylpyridinium chlorides and bromides; cationic imidazoline derivatives; and cationic amine oxides.

The thickening agents which may be incorporated into certain embodiments disclosed herein may be inorganic or organic. Among these, mention may be made of natural thickening polymers such as gums (e.g., xanthan gum, carob gum, guar gum), and synthetic thickening polymers (such as hydroxyethylcellulose and polyacrylic acids). Among these synthetic polymers, mention may be made, for example, of associative polymers comprising a fatty chain, such as associative polymers chosen from acrylic associative polymers and polyurethane associative polymers.

The pH of the dyeing composition as disclosed herein may range from 3 to 12, such as from 5 to 11 and from 6 to 10.

This pH may be adjusted to the desired value by adding to the composition acidifying or alkalinizing agents generally used in dyeing keratinous fibers, or alternatively with the aid of conventional buffer systems.

Among the acidifying agents, there may be mentioned, by way of example, inorganic or organic acids such as hydrochloric acid; orthophosphoric acid; sulphuric acid; carboxylic acids such as acetic acid, tartaric acid, citric acid, and lactic acid; and sulphonic acids.

Among the alkalinizing agents, there may be mentioned, by way of example, aqueous ammonia; alkali metal carbonates; alkanolamines such as mono-, di- and triethanolamines and derivatives thereof; sodium hydroxides; potassium hydroxides; and compounds of the following formula (V):

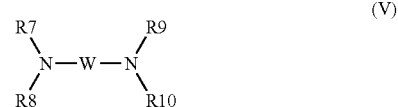

in which W is a propylene residue optionally substituted with at least one group chosen from hydroxyl groups and $C_1$-$C_4$ alkyl groups; $R_7$, $R_8$, $R_9$ and $R_{10}$, which are identical or different, are chosen from hydrogen, $C_1$-$C_4$ alkyl radicals, and $C_1$-$C_4$ hydroxyalkyl radicals.

The composition disclosed herein may be provided in various galenic forms such as a lotion, a cream, a gel or any other appropriate form for dyeing keratinous fibers. It may also be packaged under pressure in an aerosol can in the presence of a propellant and can form a mousse.

Another embodiment disclosed herein is the use of compounds of formula (I) as defined above, as a direct dye in compositions as defined above for dyeing keratinous fibers, for example human keratinous fibers, such as the hair.

Additionally, another embodiment disclosed herein is a method for the direct dyeing of keratinous fibers comprising:

a) applying to the keratinous fibers a dyeing composition as defined above;

b) leaving the composition on the keratinous fibers for a sufficient leave-in time to obtain the desired color;

c) optionally rinsing the keratinous fibers so as to remove the said dyeing composition therefrom;

d) optionally washing the keratinous fibers at least once, rinsing them after each wash; and e) optionally drying the keratinous fibers.

Thus, the direct dyeing method disclosed herein comprises a first step comprising applying to the keratinous fibers to be dyed the dyeing composition as defined above, and then, according to a second step, leaving the composition on the keratinous fibers, generally for a leave-in time ranging from 3 to 60 minutes, such as 5 to 40 minutes or 15 to 30 minutes, so as to give the composition time to act on the keratinous fibers. This leave-in phase may, for example, be carried out at a temperature ranging from room temperature to 80° C., such as from 25 to 55° C.

Next, the keratinous fibers thus dyed are optionally rinsed to remove the dyeing composition which has reacted with the fibers and optionally washed at least once.

When the dyeing composition comprises at least one compound of formula (I) and at least one oxidation dye, as mentioned above, the dyeing method may require an additional step for developing, with at least one oxidizing agent, the color of the oxidation dye.

Accordingly, disclosed herein is a method for dyeing keratinous fibers comprising:

a) applying to the keratinous fibers a dyeing composition comprising at least one compound of formula (I) as defined above and at least one oxidation dye, wherein the color of the oxidation dye is developed with at least one oxidizing agent;

b) leaving the composition on the keratinous fibers for a sufficient leave-in time to obtain the desired color;

c) optionally rinsing the keratinous fibers to remove the said dyeing composition therefrom;

d) optionally washing the keratinous fibers at least once, rinsing them after each wash; and e) optionally drying the keratinous fibers.

The at least one oxidizing agent which may be used is chosen from, for example, hydrogen peroxide; urea peroxide; alkali metal bromates; persalts such as perborates and persulphates; peracids; and oxidase enzymes such as peroxidases, oxidoreductases comprising two electrons such as uricases, and oxygenases comprising four electrons such as laccases. In certain embodiments, the oxidizing agent is hydrogen peroxide.

The at least one oxidizing agent may be added to the composition disclosed herein at the time of use or the oxidizing composition may comprise the at least one oxidizing agent.

Furthermore, the composition disclosed herein may be left on the keratinous fibers for a time period ranging from 3 to 60 minutes, such as for 5 to 40 minutes or 15 to 30 minutes, so as to give the composition enough time to act on the keratinous fibers and for the development to take place. This leave-in phase may be carried out at a temperature ranging from room temperature to 80° C., such as from 25 to 55° C.

The following examples are given by way of illustration and without limitation. Other than in the examples, or where otherwise indicated, all numbers expressing quantities of ingredients, reaction conditions, and so forth used in the specification and claims are understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical values, however, inherently contain certain errors necessarily resulting from the standard deviation found in their respective testing measurements.

EXAMPLE 1

A dyeing composition 1 in accordance with the above disclosure was prepared, having the constituents described in Table 1 below. This composition comprises a dye (1) (molecular weight: 412 g/mol) in accordance with certain embodiments disclosed herein, corresponding to the following formula:

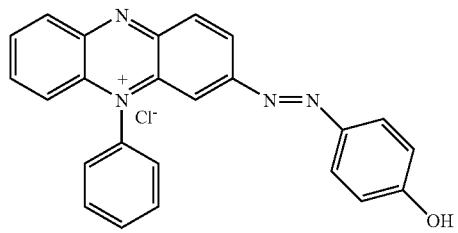

TABLE 1

| Constituents | Quantity |
| --- | --- |
| Dye (1) | 0.41 g |
| Benzyl alcohol | 4 g |
| Polyethylene glycol 6 EO | 6 g |
| Hydroxyethylcellulose | 0.7 g |
| Alkyl polyglucoside as an aqueous solution comprising 60% AM* | 4.5 g AM* |
| Phosphate buffer | qs pH 7 |
| Demineralized water | qs 100 g |

*AM: Active material.

EXAMPLE 2

A dyeing composition 2 in accordance with the above disclosure was prepared, having the constituents described in Table 2 below. This composition comprises a dye (2) (molecular weight: 499 g/mol) in accordance with certain embodiments disclosed herein, corresponding to the following formula:

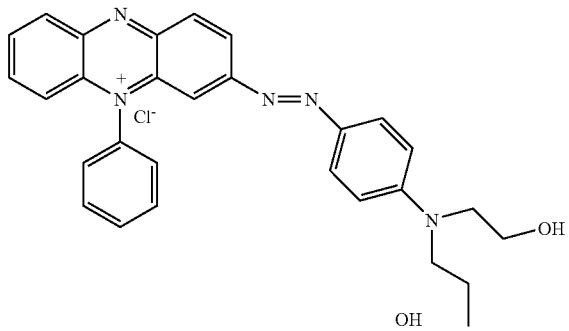

TABLE 2

| Constituents | Quantity |
| --- | --- |
| Dye (2) | 0.50 g |
| Benzyl alcohol | 4 g |
| Polyethylene glycol 6 EO | 6 g |
| Hydroxyethylcellulose | 0.7 g |

TABLE 2-continued

| Constituents | Quantity |
| --- | --- |
| Alkyl polyglucoside as an aqueous solution comprising 60% AM* | 4.5 g AM* |
| Phosphate buffer | qs pH 7 |
| Demineralized water | qs 100 g |

*AM: Active material.

EXAMPLE 3

A dyeing composition 3 in accordance with above disclosure was prepared, having the constituents described in Table 3 below. This composition comprises a dye (3) (molecular weight: 483 g/mol) in accordance with certain embodiments disclosed herein, corresponding to the following formula:

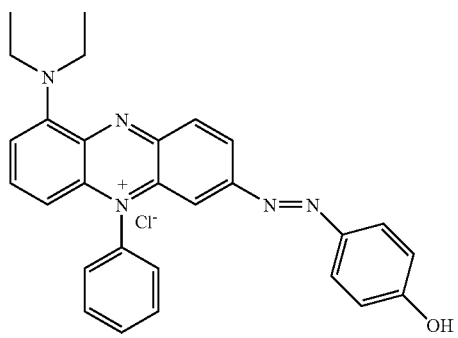

(IV)

TABLE 3

| Constituents | Quantity |
| --- | --- |
| Dye (3) | 0.48 g |
| Benzyl alcohol | 4 g |
| Polyethylene glycol 6 EO | 6 g |
| Hydroxyethylcellulose | 0.7 g |
| Alkyl polyglucoside as an aqueous solution comprising 60% AM* | 4.5 g AM* |
| Phosphate buffer | qs pH 7 |
| Demineralized water | qs 100 g |

*AM: Active material.

What is claimed is:

1. A composition for dyeing keratinous fibers, comprising an aqueous medium comprising water or a mixture of water and a cosmetically acceptable organic solvent and at least one dye chosen from the compounds of the following formula (I):

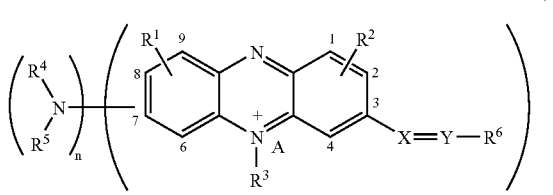

(I)

in which:
$R^1$ and $R^2$, independently of each other, are chosen from hydrogen;
alkyl groups having 1 to 6 carbon atoms, wherein said alkyl groups are optionally substituted with at least one group chosen from hydroxyl groups, amino groups, halogen groups, $C_1$ to $C_3$ alkoxy groups, and aryl groups;
aryl groups having 6 to 18 carbon atoms, wherein said aryl groups are optionally substituted with at least one group chosen from amino groups, hydroxyl groups, $C_1$ to $C_3$ alkoxy groups, and $C_1$ to $C_6$ alkyl groups;
carboxyalkyl groups having 1 to 6 carbon atoms; and
sulphoalkyl groups having 1 to 6 carbon atoms;
$R^3$ is chosen from optionally substituted alkyl groups having 1 to 6 carbon atoms, alkenyl groups having 2 to 10 carbon atoms, and cyclic groups having 5 to 100 carbon atoms, wherein said cyclic groups are aromatic or non-aromatic and optionally comprise at least one heteroatom and at least one unsaturated bond, and further wherein said cyclic group is optionally substituted with at least one group chosen from hydroxyl groups, cyano groups, halogen groups, amino groups, aryl groups, alkoxy groups, and alkyl groups having 1 to 4 carbon atoms;
$R^6$ is a group chosen from monocyclic groups and polycyclic groups, wherein said monocyclic groups and polycyclic groups have 5 to 100 carbon atoms, and further wherein said monocyclic groups and polycyclic groups optionally comprise at least one heteroatom and at least one unsaturated bond, and are optionally substituted with at least one group chosen from hydroxyl groups, cyano groups, halogen groups, amino groups, aryl groups, alkoxy groups, and alkyl groups having 1 to 4 carbon atoms;
X and Y, independently of each other, are chosen from nitrogen and CR' groups, wherein R' is chosen from hydrogen and alkyl groups having 1 to 6 carbon atoms;
A is an anionic counterion; and
n is chosen from 0 and 1;
wherein when n is equal to 1, the group of formula $R^4R^5N$— occupies a position chosen from the 1-, 6-, 8-, and 9-positions on formula (I), and $R^4$ and $R^5$, independently of each other, are chosen from hydrogen, aryl groups, and alkyl groups having 1 to 6 carbon atoms optionally substituted with at least one group chosen from hydroxyl groups, cyano groups, halogen groups, amino groups, aryl groups, and alkoxy groups having 1 to 4 carbon atoms.

2. The composition according to claim 1, wherein the group $R^3$ is an aryl group having 6 to 18 carbon atoms, optionally substituted with at least one substituent chosen from hydroxyl groups, cyano groups, halogen groups, amino groups, alkoxy groups having 1 to 4 carbon atoms, and alkyl groups having 1 to 4 carbon atoms.

3. The composition according to claim 1, wherein the group $R^6$ is an aryl group having 6 to 18 carbon atoms, optionally substituted with at least one substituent chosen from hydroxyl groups, cyano groups, halogen groups, amino groups, alkoxy groups having 1 to 4 carbon atoms, and alkyl groups having 1 to 4 carbon atoms.

4. The composition according to claim 3, wherein the group $R^6$ is chosen from phenol groups which are optionally substituted and aniline groups which are optionally substituted on at least one of the nitrogen atom and the benzene ring.

5. The composition according to claim 1, wherein X and Y each represent a nitrogen atom.

6. The composition according to claim 1, wherein the at least one dye is chosen from:

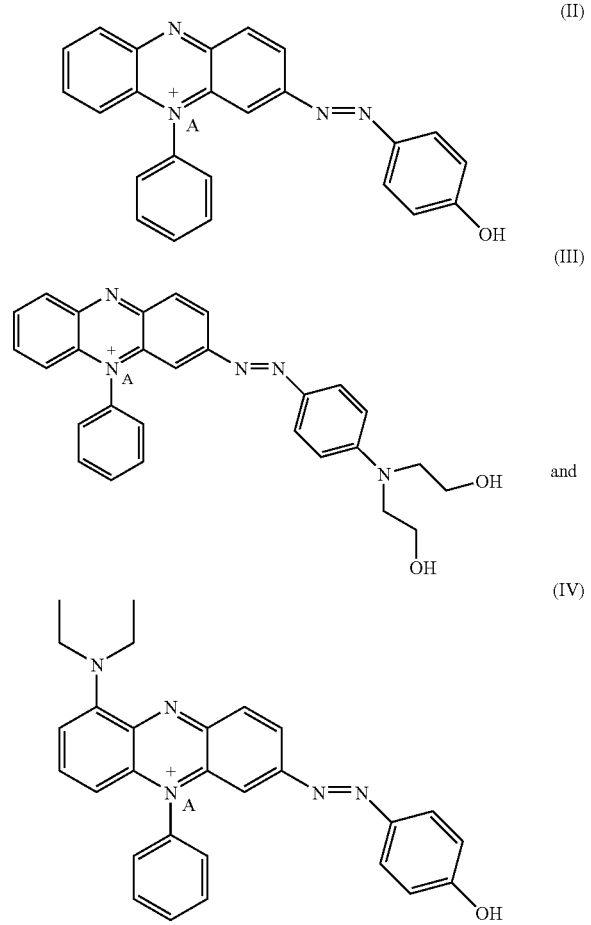

wherein A is an anionic counterion.

7. The composition according to claim 6, wherein A is a chloride anion.

8. The composition according to claim 1, wherein the at least one dye is present in the composition in an amount ranging from 0.001 to 20% by weight relative to the total weight of the composition.

9. The composition according to claim 8, wherein the at least one dye is present in the composition in an amount ranging from 0.01 to 10% by weight relative to the total weight of the composition.

10. The composition according to claim 9, wherein the at least one dye is present in the composition in an amount ranging from 0.1 to 5% by weight relative to the total weight of the composition.

11. The composition according to claim 1, wherein the said cosmetically acceptable organic solvent is an alcohol.

12. The composition according to claim 11, wherein the alcohol is chosen from ethyl alcohol, isopropyl alcohol, benzyl alcohol, polyols, polyol ethers, alkanes, ketones, and mixtures thereof.

13. The composition according to claim 1, further comprising at least one direct dye different from the compounds of formula (I).

14. The composition according to claim 13, wherein the at least one direct dye is chosen from nitro dyes, methines, azomethines, aromatic diamines, styriles, triarylmethanes, diarylmethanes, azo dyes, anthraquinone and naphthoquinone dyes, porphyrins, tetraphenylporphyrins, metalloporphyrins, phthalocyanines, carotenoid natural dyes, terpenoid natural dyes, flavonoid type natural dyes, and fluorescent dyes.

15. The composition according to claim 14, wherein the fluorescent dyes are chosen from fluoroscein, rhodamine, and coumarin.

16. The composition according to claim 1, further comprising at least one oxidation base optionally combined with at least one coupler.

17. The composition according to claim 16, wherein the at least one oxidation base is chosen from para-phenylenediamines, bisphenylalkylenediamines, para-aminophenols, ortho-aminophenols, and heterocyclic bases.

18. The composition according to claim 16, wherein the at least one coupler is chosen from meta-phenylenediamine couplers, meta-aminophenol couplers, meta-diphenol couplers, naphthalenic couplers, and heterocyclic couplers.

19. The composition according to claim 1, further comprising at least one additive chosen from surfactants, thickening agents, antioxidants, sequestering agents, dispersing agents, hair conditioners, preservatives, opacifying agents, acidifying agents, basifying agents, and perfumes.

20. The composition according to claim 1, wherein the pH ranges from 3 to 12.

21. The composition according to claim 20, wherein the pH ranges from 5 to 11.

22. The composition according to claim 21, wherein the pH ranges from 6 to 10.

23. A method of dyeing keratinous fibers comprising applying to said keratinous fibers a compound according to claim 1.

24. A method for the direct dyeing of keratinous fibers, comprising:
a) applying to the keratinous fibers a composition for dyeing keratinous fibers comprising an aqueous medium comprising water or a mixture of water and a cosmetically acceptable organic solvent and at least one dye chosen from the compounds of the following formula (I):

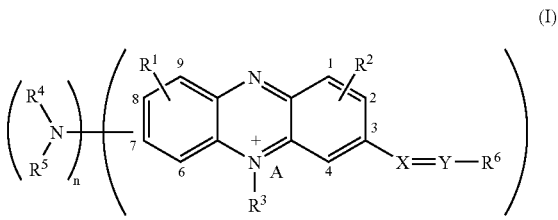

in which:
R$^1$ and R$^2$, independently of each other, are chosen from
  hydrogen;
  alkyl groups having 1 to 6 carbon atoms, wherein said alkyl groups are optionally substituted with at least one group chosen from hydroxyl groups, amino groups, halogen groups, C$_1$ to C$_3$ alkoxy groups, and aryl groups;
  aryl groups having 6 to 18 carbon atoms, wherein said aryl groups are optionally substituted with at least one group chosen from amino groups, hydroxyl groups, $C_1$ to $C_3$ alkoxy groups, and $C_1$ to $C_6$ alkyl groups;

carboxyalkyl groups having 1 to 6 carbon atoms; and sulphoalkyl groups having 1 to 6 carbon atoms;

$R^3$ is chosen from optionally substituted alkyl groups having 1 to 6 carbon atoms, alkenyl groups having 2 to 10 carbon atoms, and cyclic groups having 5 to 100 carbon atoms, wherein said cyclic groups are aromatic or non-aromatic and optionally comprise at least one heteroatom and at least one unsaturated bond, and further wherein said cyclic group is optionally substituted with at least one group chosen from hydroxyl groups, cyano groups, halogen groups, amino groups, aryl groups, alkoxy groups, and alkyl groups having 1 to 4 carbon atoms;

$R^6$ is a group chosen from monocyclic groups and polycyclic groups, wherein said monocyclic groups and polycyclic groups have 5 to 100 carbon atoms, and further wherein said monocyclic groups and polycyclic groups optionally comprise at least one heteroatom and at least one unsaturated bond, and are optionally substituted with at least one group chosen from hydroxyl groups, cyano groups, halogen groups, amino groups, aryl groups, alkoxy groups, and alkyl groups having 1 to 4 carbon atoms;

X and Y, independently of each other, are chosen from nitrogen and CR' groups, wherein R' is chosen from hydrogen and alkyl groups having 1 to 6 carbon atoms;

A is an anionic counterion; and n is chosen from 0 and 1;

wherein when n is equal to 1, the group of formula $R^4R^5N$— occupies a position chosen from the 1-, 6-, 8-, and 9-positions on formula (I), and $R^4$ and $R^5$, independently of each other, are chosen from hydrogen, aryl groups, and alkyl groups having 1 to 6 carbon atoms optionally substituted with at least one group chosen from hydroxyl groups, cyano groups, halogen groups, amino groups, aryl groups, and alkoxy groups having 1 to 4 carbon atoms;

b) leaving the composition on the keratinous fibers for a sufficient time to obtain the desired color;

c) optionally rinsing the keratinous fibers so as to remove the said dyeing composition therefrom;

d) optionally washing the keratinous fibers at least once, rinsing the keratinous fibers after each wash; and e) optionally drying the keratinous fibers.

25. A method for dyeing keratinous fibers comprising:

a) applying to the keratinous fibers a dyeing composition for keratinous fibers comprising an aqueous medium comprising water or a mixture of water and a cosmetically acceptable organic solvent and at least one oxidation dye, and at least one dye chosen from the compounds of the following formula (I):

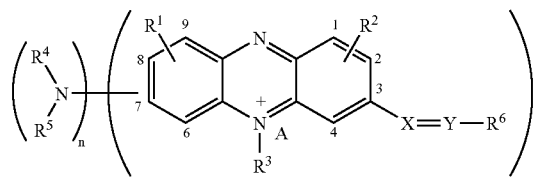

in which:

$R^1$ and $R^2$, independently of each other, are chosen from hydrogen;

alkyl groups having 1 to 6 carbon atoms, wherein said alkyl groups are optionally substituted with at least one group chosen from hydroxyl groups, amino groups, halogen groups, $C_1$ to $C_3$ alkoxy groups, and aryl groups;

aryl groups having 6 to 18 carbon atoms, wherein said aryl groups are optionally substituted with at least one group chosen from amino groups, hydroxyl groups, $C_1$ to $C_3$ alkoxy groups, and $C_1$ to $C_6$ alkyl groups;

carboxyalkyl groups having 1 to 6 carbon atoms; and sulphoalkyl groups having 1 to 6 carbon atoms;

$R^3$ is chosen from optionally substituted alkyl groups having 1 to 6 carbon atoms, alkenyl groups having 2 to 10 carbon atoms, and cyclic groups having 5 to 100 carbon atoms, wherein said cyclic groups are aromatic or non-aromatic and optionally comprise at least one heteroatom and at least one unsaturated bond, and further wherein said cyclic group is optionally substituted with at least one group chosen from hydroxyl groups, cyano groups, halogen groups, amino groups, aryl groups, alkoxy groups, and alkyl groups having 1 to 4 carbon atoms;

$R^6$ is a group chosen from monocyclic groups and polycyclic groups, wherein said monocyclic groups and polycyclic groups have 5 to 100 carbon atoms, and further wherein said monocyclic groups and polycyclic groups optionally comprise at least one heteroatom and at least one unsaturated bond, and are optionally substituted with at least one group chosen from hydroxyl groups, cyano groups, halogen groups, amino groups, aryl groups, alkoxy groups, and alkyl groups having 1 to 4 carbon atoms;

X and Y, independently of each other, are chosen from nitrogen and CR' groups, wherein R' is chosen from hydrogen and alkyl groups having 1 to 6 carbon atoms;

A is an anionic counterion; and n is chosen from 0 and 1;

wherein when n is equal to 1, the group of formula $R^4R^5N$— occupies a position chosen from the 1-, 6-, 8-, and 9-positions on formula (I), and $R^4$ and $R^5$, independently of each other, are chosen from hydrogen, aryl groups, and alkyl groups having 1 to 6 carbon atoms optionally substituted with at least one group chosen from hydroxyl groups, cyano groups, halogen groups, amino groups, aryl groups, and alkoxy groups having 1 to 4 carbon atoms;

wherein the color of the oxidation dye is developed with at least one oxidizing agent;

b) leaving the dyeing composition on the keratinous fibers for a sufficient time to obtain the desired color;
c) optionally rinsing the keratinous fibers to remove the said dyeing composition therefrom;
d) optionally washing the keratinous fibers at least once, rinsing the keratinous fibers after each wash; and
e) optionally drying the keratinous fibers.

26. The method according to claim 24, wherein the dyeing composition is left on the keratinous fibers for a time ranging from 3 to 60 minutes.

27. The method according to claim 26, wherein the dyeing composition is left on the keratinous fibers for a time ranging from 5 to 40 minutes.

28. The method according to claim 27, wherein the dyeing composition is left on the keratinous fibers for a time ranging from 15 to 30 minutes.

29. The method according to claim 25, wherein the dyeing composition is left on the keratinous fibers for a time ranging from 3 to 60 minutes.

30. The method according to claim 29, wherein the dyeing composition is left on the keratinous fibers for a time ranging from 5 to 40 minutes.

31. The method according to claim 30, wherein the dyeing composition is left on the keratinous fibers for a time ranging from 15 to 30 minutes.

32. The method according to claim 25, wherein the oxidizing agent is chosen from hydrogen peroxide, urea peroxide, alkali metal bromates, persalts, peracids, and oxidase enzymes.

33. The method according to claim 32, wherein the persalts are chosen from perborates and persuiphates.

34. The method according to claim 32, wherein the oxidase enzymes are chosen from peroxidases, oxidoreductases comprising two electrons, and oxygenases comprising four electrons.

35. The method according to claim 34, wherein the oxidoreductases comprising two electrons are chosen from uricases.

36. The method according to claim 34, wherein the oxygenases comprising four electrons are chosen from laccases.

* * * * *

UNITED STATES PATENT AND TRADEMARK OFFICE
CERTIFICATE OF CORRECTION

PATENT NO.       : 7,326,257 B2
APPLICATION NO.  : 10/902087
DATED            : February 5, 2008
INVENTOR(S)      : Alain Lagrange et al.

It is certified that error appears in the above-identified patent and that said Letters Patent is hereby corrected as shown below:

Column 18, line 10, "persuiphates." should read --persulphates.--.

Signed and Sealed this

Third Day of June, 2008

JON W. DUDAS
*Director of the United States Patent and Trademark Office*